US007199594B2

(12) United States Patent
Kermani

(10) Patent No.: US 7,199,594 B2
(45) Date of Patent: Apr. 3, 2007

(54) BIOSENSOR APPARATUS AND METHOD WITH SAMPLE TYPE AND VOLUME DETECTION

(75) Inventor: Mahyar Zardoshti Kermani, Pleasanton, CA (US)

(73) Assignee: LifeScan, Inc., Milpitas, CA (US)

(*) Notice: Subject to any disclaimer, the term of this patent is extended or adjusted under 35 U.S.C. 154(b) by 0 days.

(21) Appl. No.: 11/036,658

(22) Filed: Jan. 13, 2005

(65) Prior Publication Data
US 2006/0119362 A1 Jun. 8, 2006

Related U.S. Application Data

(62) Division of application No. 10/020,169, filed on Dec. 12, 2001, now Pat. No. 6,856,125.

(51) Int. Cl.
*G01R 27/26* (2006.01)
(52) U.S. Cl. .................... 324/663; 324/71.1
(58) Field of Classification Search .............. 73/290, 73/149; 324/71.1, 692, 663, 171.1; 702/182; 205/777.5; 600/347
See application file for complete search history.

(56) References Cited

U.S. PATENT DOCUMENTS

| 4,316,381 | A | * | 2/1982 | Woodruff | .................... | 73/31.05 |
| 5,172,065 | A | * | 12/1992 | Wallrafen | .................... | 324/683 |
| 5,245,869 | A | * | 9/1993 | Clarke et al. | ................. | 73/149 |
| 5,494,831 | A | | 2/1996 | Kindler | | |
| 5,615,672 | A | * | 4/1997 | Braig et al. | ................. | 600/474 |
| 6,051,422 | A | | 4/2000 | Borkholder et al. | | |
| 6,193,873 | B1 | | 2/2001 | O'hara et al. | | |
| 6,248,080 | B1 | | 6/2001 | Miesel et al. | | |
| 6,645,368 | B1 | * | 11/2003 | Beaty et al. | ................. | 205/792 |

(Continued)

FOREIGN PATENT DOCUMENTS

WO       WO 97/18465       5/1997

(Continued)

OTHER PUBLICATIONS

European Search Report dated Oct. 26, 2005 for EP 05 07 7178.

(Continued)

*Primary Examiner*—Walter Benson
(74) *Attorney, Agent, or Firm*—Kagan Binder, PLLC

(57) ABSTRACT

A biosensor apparatus and method with sample type and cell volume detection. The apparatus includes a sine wave generator to apply an AC signal to a biosensor cell containing a sample, a current-to-voltage converter, a phase shifter, a square wave generator, a synchronous demodulator, and a low pass filter which yields a signal proportional to the effective capacitance across the biosensor cell, which is proportional to the volume of the sample. In addition, the current-to-voltage converter yields a signal indicative of the type of sample contained within the biosensor cell. The method includes applying a sine wave to the biosensor cell, shifting the phase of the resultant signal, generating a square wave synchronous with the sine wave, demodulating the resultant signal with the square wave, and filtering the demodulated signal to produce a signal proportional to the effective capacitance across the biosensor cell. The biosensor apparatus and method are capable of determining sample type and measuring glucose levels over a wide range of sample volumes.

3 Claims, 8 Drawing Sheets

U.S. PATENT DOCUMENTS

| | | |
|---|---|---|
| 6,749,740 B2 * | 6/2004 | Liamos ........................ 205/792 |
| 6,797,150 B2 * | 9/2004 | Kermani et al. ......... 205/777.5 |
| 6,872,298 B2 * | 3/2005 | Kermani .................. 205/777.5 |
| 2005/0059872 A1 | 3/2005 | Shartle et al. |
| 2005/0099188 A1 * | 5/2005 | Baxter ........................ 324/678 |

FOREIGN PATENT DOCUMENTS

| | | |
|---|---|---|
| WO | WO 97/039343 | 10/1997 |
| WO | WO 98/35225 | 8/1998 |
| WO | WO 99/32881 | 7/1999 |
| WO | WO 99/45387 | 9/1999 |
| WO | WO 99/56613 | 11/1999 |
| WO | WO 00/20626 | 4/2000 |
| WO | WO 00/57177 | 9/2000 |
| WO | WO 01/33216 | 5/2001 |
| WO | WO 01/88518 | 11/2001 |

OTHER PUBLICATIONS

Kolle, C., et al., "Low-Cost, High-Precision Measurement System for Capacitive Sensors", Measurement Science and Technology, IOP Publishing, Bristol, GB, vol. 9, No. 3, Mar. 1998 pp. 510-517.

Kolle, et al., "Low-Cost, High-Precision Measurement System for Capacitive Sensors," (1998) IOP Publishing, Bristol, Great Britain, 9(3):510-517.

Min, et al., "Lock-in Measurement of Bio-Impedance Variations," (2000) Measurement, Institute of Measurement and Control, London, Great Britain, 27(1):21-28.

Baxter, "Capacitive Sensors," (1997) IEEE Press, p. 54.

* cited by examiner

BIOSENSOR APPARATUS AND METHOD WITH SAMPLE TYPE AND VOLUME DETECTION

CROSS-REFERENCE TO RELATED PATENT APPLICATIONS

This application is a divisional of U.S. patent application Ser. No. 10/020,169, filed on Dec. 12, 2001, now U.S. Pat. No. 6,856,125 herein incorporated by reference in its entirety.

FIELD OF THE INVENTION

The present invention relates to biosensors and, more particularly, to a method and apparatus for detecting the type and volume of samples deposited within a biosensor cell.

BACKGROUND OF THE INVENTION

A biosensor is a device that measures the presence of various chemical components in a sample deposited in a biosensor cell. For example, a biosensor may be used to measure the amount of glucose present in a sample of blood. Generally, the biosensor cell includes a pair of conductors, e.g., gold and palladium, configured to receive a sample therebetween. Typically, the biosensor generates an electrical signal that is proportional to the amount of a certain component, e.g., glucose, in a sample, which is assumed to have a certain volume. If the sample is too small/large, however, the electrical signal will indicate a concentration which is lower/higher than the actual concentration of the component in the sample, resulting in the potential for improper diagnosis and treatment. Accordingly, methods and apparatus for determining the adequacy of a biological sample are useful.

One method for determining the adequacy of a sample within a biosensor cell is through the use of electric sensors. The electric sensors are conductors that detect the flow of electricity. In this method one or more detection conductors are positioned at different locations throughout the biosensor cell. When the sample comes in contact with a detection conductor, the detection conductor will conduct electricity, thereby indicating the presence of the sample at the location. Electronic circuitry can then be used to determine whether an adequate sample has been deposited into the biosensor cell based on the number of detection conductors that conduct electricity. This method has several drawbacks. First, several detection conductors are required in addition to the two existing parallel plate conductors of the biosensor cell. Second, an error is introduced if the sample touches a detection conductor without filling the area of the conductor completely. Third, this method is not able to compensate for bubbles trapped within the sample, which reduces the volume of the sample.

Another method for determining the adequacy of a sample applied to a biosensor cell is through visual confirmation of the sample volume. In this method, the user of the device visually inspects the sample within the biosensor to determine if a sufficient sample has been applied to the biosensor. This method relies on a subjective determination of the volume of a sample and is, therefore, prone to errors. This is especially problematic when the biosensor is used to measure chemical components associated with certain diseases, such as diabetes, that cause decreased visual acuity in the user.

The prior art methods used to determine the adequacy of a sample result in the test being performed only if the sample volume is within a narrow range. If the sample volume is outside of this range, the test is aborted. This "go/no-go" method of using biological samples, which relies on the sample volume being within a narrow range, results in wasted time and samples for samples outside this narrow range.

Therefore, there is a need for apparatus and methods to accurately determine the volume of a sample within a biosensor cell and to determine chemical component concentrations for a wide range of sample volumes. The present invention fulfills this need among others.

SUMMARY OF THE INVENTION

The present invention provides for apparatus and methods that can determine whether a sufficient sample volume was deposited into a biosensor, can accommodate variations in the volume of samples, and can determine the type of sample deposited within the biosensor. The aforementioned problems are overcome by accurately detecting the volume of the sample within the biosensor cell by determining the biosensor cell's effective capacitance, which is proportional to the volume of the sample within the biosensor cell.

One aspect of the present invention is an apparatus for measuring the effective capacitance across a biosensor cell having a first conductor connection and a second conductor connection, the biosensor cell configured to receive a sample having a volume related to the effective capacitance across the biosensor cell. The apparatus includes a sine wave generator having an output for coupling to the first conductor connection of the biosensor cell, the sine wave generator producing an AC signal, a current-to-voltage (I/V) converter having an input for coupling to the second conductor of the biosensor cell and further having an output, a phase shifter having an input coupled to the output of the I/V converter and further having an output, a square wave generator producing a square wave synchronous with the AC signal, a synchronous demodulator having an output, a first input coupled to the phase shifter, and a second input coupled to the square wave generator, and a low pass filter (LPF) having an input coupled to the output of the synchronous demodulator, the LPF producing a signal at an output proportional to the effective capacitance across the biosensor cell.

Another aspect of the invention is a method for measuring the effective capacitance across a biosensor cell having a first conductor connection and a second conductor connection, the biosensor cell configured for use in a biosensor to receive a sample having a volume. The method includes applying a sine wave having a frequency to the first conductor of the biosensor cell to produce an AC signal, shifting the phase of the AC signal, generating a square wave synchronous with the sine wave, demodulating the AC signal with the square wave to produce a demodulated signal, and filtering the demodulated signal to produce a signal proportional to the effective capacitance across the biosensor cell.

DETAILED DESCRIPTION OF THE INVENTION

Figure 1:
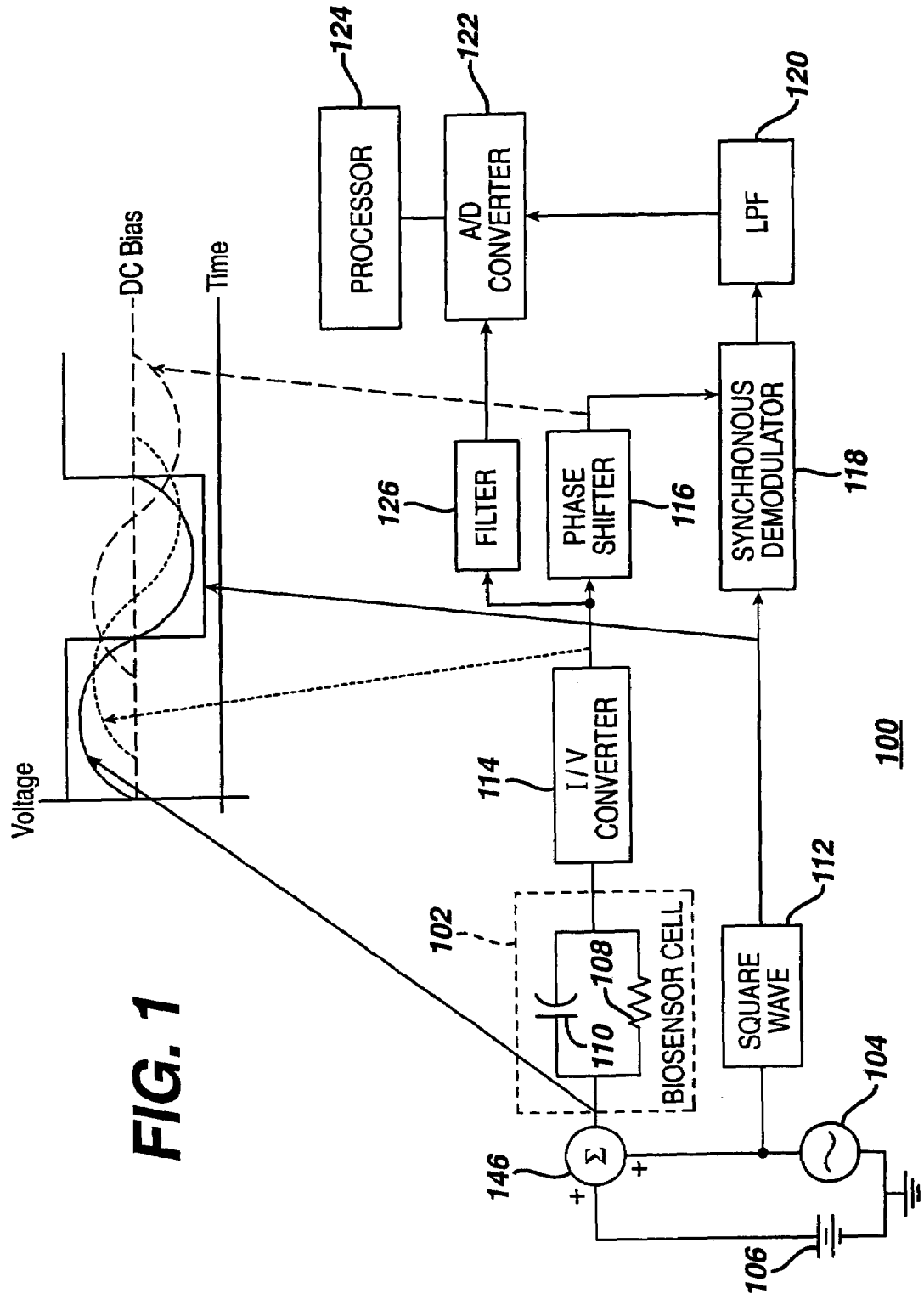
FIG. 1 is a block diagram of a biosensor and associated signal levels in accordance with the present invention.

FIG. 1 is a block diagram of biosensor device 100 in accordance with one embodiment of the present invention for determining the volume of a sample positioned within a biosensor cell 102 and the type of sample positioned within the biosensor cell 102. In addition, FIG. 1 depicts signal levels developed at various locations within the biosensor device 100. In a general overview, an AC sine wave generated by an AC sine wave generator 104 and a DC biasing voltage generated by a DC voltage source 106 are combined by a combiner 146 and applied to the biosensor cell 102 to create a signal that reflects the effective resistance 108 and capacitance 110 across the biosensor cell 102. In addition, the AC sine wave is passed to a square wave generator 112 that generates a square wave synchronous with the sine wave. The signal out of the biosensor cell 102 is passed through a current-to-voltage (I/V) converter 114 to convert the signal to a voltage signal. The voltage signal out of the I/V converter 114 is phase shifted by a phase shifter 116. The output of the phase shifter 116 is passed to a synchronous demodulator 118 for demodulation using the output of the square wave generator 112 to create a demodulated signal. The demodulated signal is passed through a LPF 120 to create a signal proportional to the effective capacitance of the biosensor cell 102, which is proportional to the volume of the sample. The signal is converted to digital by A/D converter 122 and the digital signal is processed by a processor 124 to determine the volume of the sample based on the effective capacitance across the biosensor cell 102. In addition, the output of the I/V converter 114 is passed through a filter 126 that removes an AC sine wave component and the resultant signal is converted to digital by the A/D converter 122 for processing by the processor 124 to determine the type of sample, e.g., test sample or biological sample, applied to the biosensor cell 102. The present invention is particularly useful, but not exclusively so, in glucose measurement systems used by diabetics to determine glucose levels in samples of blood.

Figure 2:
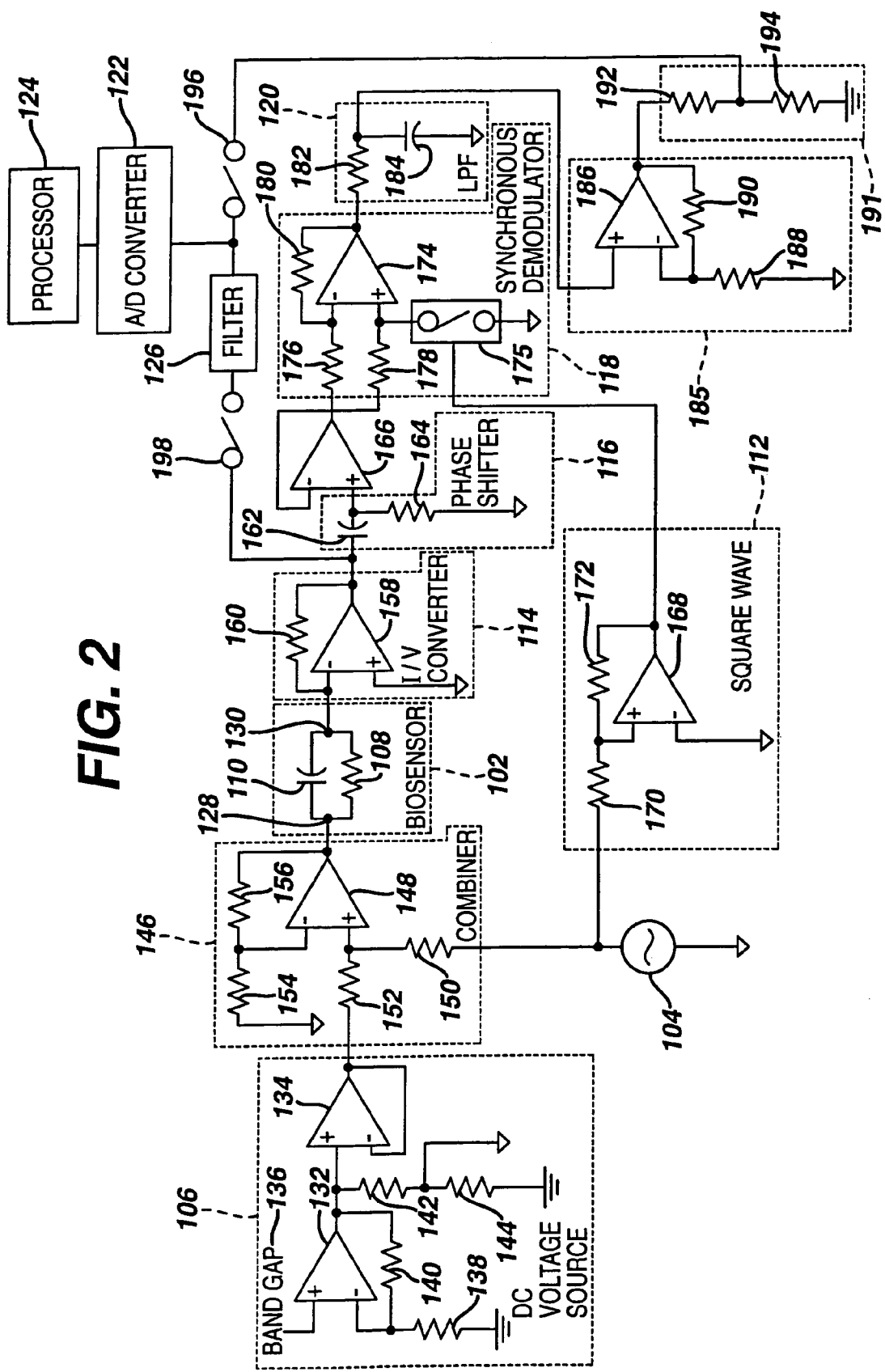
FIG. 2 is a schematic diagram of a biosensor in accordance with the present invention.

FIG. 2 is a schematic depiction of a device for determining the volume and type of a sample positioned within a biosensor cell 102 that will be used to describe an embodiment of the present invention in detail. The biosensor cell 102 is a receptacle for a sample, e.g., blood. The biosensor cell 102 may be modeled in a known manner by an effective resistance 108 in parallel with an effective capacitance 110 between a first conductor connection 128 and a second conductor connection 130 of the biosensor cell 102. The biosensor cell 102 includes a first conductor coupled to the first conductor connection 128 and a second conductor coupled to the second conductor connection 130. The first and second conductors may be a pair of parallel plates substantially parallel to one another configured to receive a sample therebetween. When a sample is positioned within the biosensor cell 102, the effective capacitance 110 of the biosensor cell 102 will be proportional to the volume of the sample. In alternative embodiments, the first and second conductors may be a pair of plates positioned on the same plane to receive a sample thereon or may be a pair of cylindrical conductors coaxial to one another configured to receive a sample therebetween.

The sine wave generator 104 generates a sine wave that can be applied to the biosensor cell 102. By applying the sine wave to the biosensor cell 102 at a first conductor connection 128, a signal is developed at the second conductor connection 130 that reflects the effective resistance 108 and capacitance 110 of the biosensor cell 102. The amplitude of the synthesized sine wave is selected such that it does not affect the electrochemical reaction in the biosensor cell 102 and can create a signal well above the system noise level. The frequency of the synthesized sine wave is selected to maximize the signal to noise ratio of the biosensor. In one embodiment, the sine wave has an amplitude of about 50 mV and a frequency of about 109.065 Hz. An example of a suitable sine wave generator is a known direct digital synthesis (DDS) chip, which includes a counter and a sine digital-to-analog (D/A) converter incorporated into an application specific integrated circuit (ASIC), such as DDS chip part number AD9832 produced by Analog Devices, Inc. of Norwood, Mass., USA. This arrangement results in a very stable "stair-type" sine wave.

The DC voltage source 106 generates a DC voltage that can be applied to the biosensor cell 102. The DC voltage enables the effective capacitance 110 to be developed quickly across the biosensor cell 102, thereby permitting the volume of the sample applied within the biosensor cell 102 to be determined quickly. In one embodiment, the DC voltage has an amplitude of about negative (−) 300 mV. The volume of the sample within the biosensor cell 102 can be determined accurately without applying the DC voltage to the biosensor cell 102. However, applying the DC voltage enables the effective capacitance 110 to be formed more quickly. Accordingly, the DC voltage source 106 may be removed from the illustrated biosensor without departing from the spirit and scope of the present invention, however, its inclusion can positively affect the performance of the biosensor in determining the effective capacitance 110.

In the illustrated embodiment, the DC voltage source 106 comprises a first conventional OpAmp 132 and a second conventional OpAmp 134. The non-inverting input of the first OpAmp 132 is coupled to a bandgap voltage 136. The bandgap voltage 136 is generated by a known bandgap circuit that generates a stable voltage from a voltage source, e.g., a battery. The bandgap voltage 136 remains constant regardless of fluctuations in the output voltage of the voltage source. The first OpAmp 132 is configured as a gain stage with its inverting input coupled to ground through a ground resistor 138 and its output coupled to its inverting input through a feedback resistor 140. In addition, the output of the first OpAmp 132 is coupled to a virtual ground through a first ground resistor 142 and to a system ground through the first ground resistor 142 and a second ground resistor 144. The non-inverting input of the second OpAmp 134 is coupled to the output of the first OpAmp 132. The second OpAmp 134 is configured as a buffer stage with its output coupled to its inverting input the output of the second OpAmp 134 reflects the DC voltage of the DC voltage source 106.

A combiner 146 combines the sine wave from the sine wave generator 104 and the DC voltage signal from the DC voltage source 106 to create a signal to apply to a first conductor connection 128 of the biosensor cell 102. In the illustrated embodiment, the combiner 146 comprises a conventional OpAmp 148. The non-inverting input of the OpAmp 148 is coupled to the sine wave generator 104 through a first input resistor 150 and to the DC voltage source 106 through a second input resistor 152. The inverting input of the OpAmp 148 is coupled to a virtual ground through a ground resistor 154 and the output of the OpAmp 148 is coupled to the non-inverting input of the OpAmp 148 through a feedback resistor 156. It will be understood by those skilled in the art that, if the DC voltage source 106 is not used, the combiner 146 may be removed and the sine wave generator 104 can be coupled directly to the biosensor cell 102.

The I/V converter 114 receives the current signal out of the biosensor cell 102 and converts it to a voltage signal. In the illustrated embodiment, the I/V converter comprises a conventional OpAmp 158. The inverting input of the OpAmp 158 is connected to the second conductor connection 130 of the biosensor cell 102. The non-inverting input of the OpAmp 158 is connected to a virtual ground. A feedback resistor 160 coupled between the output of the OpAmp 158 and the inverting input defines the gain of the I/V converter 114.

The phase shifter 116 shifts the phase of a signal out of the I/V converter 114 and, if present, removes any DC component from the signal. In one embodiment, the phase of the signal out of the I/V converter 114 is shifted 90°. In the illustrated embodiment, the phase shifter 116 comprises a capacitor 162 and resistor 164, and is followed by a buffer amplifier 166. The buffer amplifier 166 may be a conventional OpAmp with the output of the buffer amplifier 166 coupled to the inverting input of the buffer amplifier 166. The capacitor 162 is coupled between the output of the OpAmp 158 of the I/V converter 114 and the non-inverting input of the buffer amplifier 166. The resistor 164 is coupled on one end between the capacitor 162 and the non-inverting input of the buffer amplifier 166 and to a virtual ground on the other.

The square wave generator 112 generates a square wave at an output that is synchronous with the sine wave generated by the sine wave generator 104. In one embodiment, the square wave will have a comparatively low value when the sine wave produced by the sine wave generator 104 is in a negative cycle and will have comparatively high value when the sine wave is in a positive cycle. In the illustrated embodiment, the square wave generator 112 comprises a conventional OpAmp 168 configured as a Schmidt trigger with some hysteresis and is coupled to the sine wave generator 104 to generate a square wave synchronous with the sine wave produced by the sine wave generator 104. The non-inverting input of the OpAmp 168 is coupled to the sine wave generator 104 through an input resistor 170. The inverting input of the OpAmp 168 is coupled to a virtual ground. The output of the OpAmp 168 is coupled to the non-inverting input of the OpAmp 168 through a feedback resistor 172. It is contemplated that, if the sine wave generator 104 is an ASIC including a DDS chip, the square wave can be generated by the ASIC, thereby removing the need for a separate component, e.g., square wave generator 112, to generate the square wave.

The synchronous demodulator 118 is a circuit for demodulating the phase shifted signal received from the phase shifter 116 using the square wave from the square wave generator 112. The output of the synchronous demodulator 118 is a signal with a sign dependent on the comparative amplitude of the square wave produced by the square wave generator 112. If the square wave amplitude is low (indicating the sine wave is in a negative cycle), the sign of the signal will change. If the square wave amplitude is high (indicating the sine wave is in a positive cycle), the sign of the signal will not change.

In the illustrated embodiment, the synchronous demodulator 118 comprises an OpAmp 174 and a switch 175, e.g., a transistor. The inverting input and the non-inverting input of the OpAmp 174 are coupled to the output of the buffer amplifier 166 through a first input resistor 176 and a second input resistor 178, respectively. The output of the OpAmp 174 is coupled to the inverting input of the OpAmp 174 through a feedback resistor 180. In addition, the non-inverting input of the OpAmp 174 can be coupled to a virtual ground via the switch 175, which is controlled by the square wave generator 112. When the square wave amplitude is high, the switch 175 is on and the non-inverting input of the OpAmp 174 is coupled to the virtual ground, thereby changing the sign of the signal at the output of the OpAmp 174. When the square wave amplitude is low, the switch is off and the non-inverting input of the OpAmp 174 is not coupled to the virtual ground, thereby leaving the sign of the signal at the output of the OpAmp 174 unchanged.

The LPF 120 filters the output of the synchronous demodulator 118 to generate a DC signal that is proportional to the effective capacitance 110 of the biosensor cell 102, which, in turn, is proportional to the volume of a sample within the biosensor. In one embodiment, the "cut-off" frequency of the LPF 120 is much lower than the frequencies in the signal out of the synchronous demodulator 118. Since the cut-off frequency is much lower than the frequencies in the signal out of the synchronous demodulator 118, the LPF 120 averages the signal. The resultant signal is a DC signal proportional to the effective capacitance 110 of the biosensor cell 102. Support showing that the resultant signal is proportional to the effective capacitance 110 and does not represent the effective resistance 108 is described below in reference to equations 1–8. In the illustrated embodiment, the LPF 120 includes a resistor 182 and a capacitor 184. The resistor 182 is coupled on one end to the output of the synchronous demodulator 118 and to the capacitor 184 on the other. The capacitor 184 is coupled between the resistor 182 and a virtual ground.

An amplifier 185 amplifies the output of the LPF 120. In the illustrated embodiment, the amplifier 185 is a conventional OpAmp 186. The non-inverting input of the OpAmp 186 is coupled to the LPF 120. The inverting input of the OpAmp 186 is coupled to a virtual ground through a ground resistor 188 and the output of the OpAmp 186 is coupled to the inverting input of the OpAmp 186 through a feedback resistor 190.

A voltage divider 191 reduces the voltage level out of the amplifier 185 to a suitable level for the A/D converter 122. In the illustrated embodiment, the voltage divider 191 comprises a first resistor 192 and a second resistor 194 coupled in series between the output of the OpAmp 186 and a system ground. The connection between the resistors 192, 194 provides a reduced voltage level that is dependent on the values selected for the resistors 192, 194.

The filter 126 is a conventional filter for removing an AC component from the signal out of the I/V converter 114. The resultant signal out of filter 126 is indicative of the type of sample applied to the biosensor cell 102. For example, in measuring glucose levels in blood, a test sample, e.g., sugar water, is first applied to the biosensor cell 102 to determine if the biosensor is operating properly. The resultant signal can be used in a known manner to determine the type of sample, e.g., blood or sugar water. In one embodiment, the filter 126 is configured to remove AC signal frequencies equivalent to the AC signal frequency generated by the sine wave generator 104. In an alternative embodiment, the filter 126 removes all AC signals.

The A/D converter 122 converts analog signals received at an input to digital signals at an output. In one embodiment, the A/D converter 122 is coupled to the LPF 120 through the voltage divider 191 and amplifier 185 via a switch 196, e.g., a transistor, to perform a first function of converting the signal proportional to the effective capacitance 110 of the biosensor cell 102 from analog to digital. In addition, the A/D converter 122 may be coupled to the output of the I/V converter 114 through the filter 126 via a switch 198, e.g., another transistor, to perform a second function of converting the signal indicative of the type of sample within the biosensor cell 102 from analog to digital. The closure of the switches 196, 198 is mutually exclusive to prevent more than one signal from entering the A/D converter 122 at a time. It will be understood by those skilled in the art that the A/D conversion for determining the effective capacitance 110 of the biosensor cell 102 and the A/D conversion for determining the type of sample deposited within the biosensor cell 102 can be performed by two separate A/D converters. If separate A/D converters are used, or if only one function is to be performed, the switches 196, 198 can be eliminated.

In one embodiment, the A/D converter 122 is a dual slope A/D converter. A dual slope A/D converter is a device that converts analog signals to digital by integrating the analog signal for a specified period of time and, then, counting time intervals to bring the integrated signal back to zero. The counted time intervals are the basis for the digital signal output by the dual slope A/D converter. It will be understood by those skilled in the art that the integration time of the dual slope A/D converter can be selected to reject the AC frequency generated by the sine wave generator 104, thereby effectively removing the AC signal out of the I/V converter 114 and eliminating the need for a separate filter 126. In one embodiment, the integration time is selected to reject a 60/50 Hz line interference, e.g., 18.34 mSec. In addition, the frequency of the sine wave generated by the sine wave generator 104 is selected to have the maximum attenuation at the selected integration time of 18.34 mSec, e.g., 109.065 Hz.

In the illustrated embodiment, the A/D converter 122 converts the DC signal proportional to the effective capacitance 110 of the biosensor cell 102 rather than converting the voltage and current out of the biosensor cell 102 and then determining the effective capacitance 110. This allows a slower A/D converter 122 to be used, such as the dual slope A/D converter in the above embodiment, than would be required to digitize the voltage and current out of the biosensor cell 102.

The processor 124 processes the digital signals out of the A/D converter 122. When the processor 124 is coupled to the output of the I/V converter 114 through the switch 198, the filter 126, and the A/D converter 122, the processor 124 is configured in a known manner to determine if the sample within the biosensor cell 102 is of a first type or a second type. When the processor 124 is coupled to the output of the LPF 120 through the amplifier 185, the voltage divider 191, the A/D converter 122, and the switch 196, the processor 124 is configured to determine the volume of the sample within the biosensor cell 102. Since it can be shown that the output of the LPF 120 is proportional to the volume of the sample within the biosensor, the volume of the sample can be determined using known processing techniques. The processor 124 includes, but is not limited to, microprocessors, microcontrollers, digital signal processors (DSPs), state machines, general purpose processors, specific purpose processors, application specific integrated circuits (ASICs), or essentially any apparatus capable of processing a digital signal.

In one embodiment, the processor will determines if the volume of the sample is adequate by comparing the determined volume to a predetermined value. If the sample volume is adequate, a component measurement using the sample is performed. If the sample volume is inadequate, a component measurement is not performed and an error message may be displayed to a user of the biosensor. In certain embodiments, the processor 124 will store component measurements for a sample if the sample is of a first type and discard measurements for a sample of a second type. For example, in a glucose measurement system, if the processor 124 determines that the sample type is blood, the processor 124 stores the glucose measurement. However, if the processor determines that the sample type is sugar water (a common substance used to verify the proper operation of a glucose meter), the glucose measurement is discarded.

The processor 124 may be configured to determine the amount of a component within a sample within a biosensor cell 102. For example, the processor 124 may be used to determine the amount of glucose within a sample of blood. In order to determine a glucose level in a sample, the processor 124 is coupled to the output of the I/V converter 114 through the switch 198. The voltage applied to the biosensor cell 102 by the DC voltage source 106, e.g., negative (−) 300 mV, generates a "first pulse" current, $i_{fp}$, through the biosensor cell 102. The DC voltage source 106 is then modified in a known manner to apply a voltage having an opposite polarity, e.g., positive (+) 300 mV, and allowed to settle to generate a "steady state" pulse current, $i_{ss}$, through the biosensor cell 102. In one embodiment, the glucose level for the sample may be determined by the processor 124 as described in reference to equations 9–18 below in which the pulse currents are determined and compensated based on the effective capacitance 110 of the biosensor cell 102 prior to calculating the glucose level. In an alternative embodiment, the processor 124 may determine the glucose level in a known manner based on the pulse currents and then compensate for the glucose level using the effective capacitance 110.

To reduce the effects of the variability of the electronic components within the biosensor depicted in FIG. 2, a calibration procedure is used. The calibration procedure includes averaging digital signals proportional to the effective capacitance 110 of an empty biosensor cell 102 and for a known capacitance coupled across the biosensor cell 102, and calculating a capacitance conversion slope by dividing the value obtained with the known capacitance by the difference between the value obtained with an empty biosensor cell 102 and the value obtained with the known capacitance. The capacitance conversion slope is then stored for access by the processor 124 to correct the signal proportional to the effective capacitance 110 across the biosensor cell 102.

In one embodiment, a known capacitor with a standard value, e.g., 0.47 uF±2%, is selected. The capacitance value of the capacitor is measured using a known calibrated meter, e.g., an Agilent LCR meter. The capacitor is then connected between the conductor connections 128, 130 where the biosensor cell 102 is connected to the biosensor and A/D readings out of the A/D converter 122 are recorded. The A/D readings and the known measured capacitance are used to develop a single point calibration to determine the capacitance conversion slope, which may be stored in nonvolatile memory for access by the processor 124. During operation, A/D readings of the A/D converter 122 are converted into capacitance values by the processor 124 using the stored capacitance conversion slope.

Support

When two parallel plates with the surface area of A are separated by a distance, d, with an insulator therebetween, the capacitance is calculated by:

$$Cap = \varepsilon_r \varepsilon_0 \frac{A}{d} \quad (1)$$

where is the permittivity or dielectric constant of the free space and is the relative dielectric constant of the insulator inserted between the two plates. The capacitance is directly proportional to the surface area, A, (or the electrode surface in contact with the sample solution) and is inversely proportional to the distance, d, between the two plates.

In order to generate a signal proportional to the applied sample volume, the measurement must be independent of the effective resistance 108. To prove that the output of the circuit described in reference to FIG. 2 is proportional to the biosensor cell's effective capacitance 110 and is not a function of the biosensor cell's effective resistance 108, it is assumed that the synthesized sine wave is a continuous sine wave with an amplitude, V, and frequency, f,:

$$v = V \sin \omega t, \quad (2)$$

where $\omega = 2\pi f$, and t is time. The current through the biosensor cell 102 when a sample is applied to it will have the same shape with a $\Phi$ degrees phase shift:

$$i = I \sin(\omega t + \phi) \quad (3)$$

where, $I = \{V|*Z^*\}$, $\Phi = \tan^{-1}(\omega RC)$. The impedance, Z, of the biosensor cell is:

$$Z = \frac{R}{1 + j\omega RC}. \quad (4)$$

The output of the LPF 120, $V_o$, is the average of the I/V converter 114 output after it has been phase shifted 90 degrees:

$$V_o = 2f \frac{V}{|Z|} R_s \int_0^{\frac{1}{2f}} \cos(2\pi ft + \varphi) \, dt, \quad (5)$$

where $R_S$ is the sense resistor for the I/V converter 114. In this equation, it is assumed that the phase shifter gain is one. By substituting Z and evaluating the integral:

$$V_o = 2f \frac{VR_s\sqrt{1 + \omega^2 R^2 C^2}}{R} \cdot \frac{1}{2\pi ft} [\sin(2\pi ft + \varphi)]_0^{\frac{1}{2f}}; \quad (6)$$

and $$V_o = \frac{2VR_s\sqrt{1 + \omega^2 R^2 C^2}}{\pi R} \sin(\varphi), \, \varphi = \tan^{-1}(\omega RC). \quad (7)$$

After some mathematical simplifications:

$$V_o = \frac{2V\omega R_s}{\pi} C. \quad (8)$$

Therefore, the output voltage, $V_O$, is a linear function of the biosensor cell's effective capacitance 110 and is not a function of the biosensor cell's effective resistance 108. Thus, by measuring and knowing the voltage, frequency, and sense resistor values, the biosensor cell's effective capacitance 110 can be determined, which, in turn, is an indicator of the sample volume.

Figure 3:
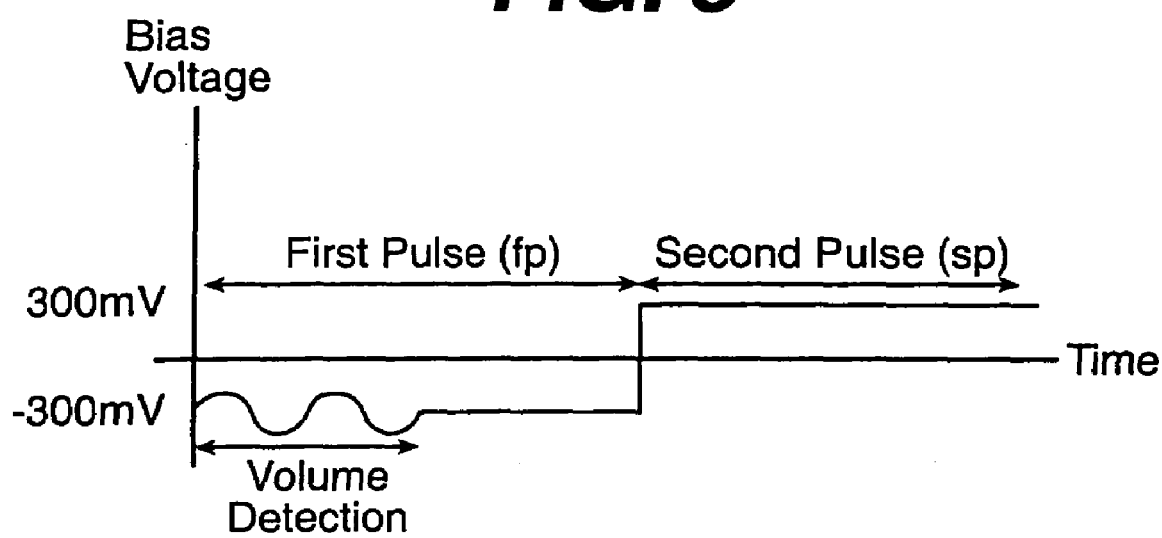
FIG. 3 is a timing diagram for measuring sample volumes and glucose levels in accordance with the present invention.

In accordance with one embodiment of the present invention, an accurate glucose measurement can be determined, even when a non-optimal sample volume is applied to the biosensor 102. FIG. 3 is a timing diagram that will be used to illustrate the development of the signals used to measure glucose levels. During a first pulse (fp) having a first DC bias voltage, e.g., −300 mV, an effective capacitance level indicative of a sample volume is detected during a volume detection period in which an AC signal is applied to the sample. Also during the first pulse, after the AC signal is removed, a first current level through the biosensor cell 102 is measured. During a second pulse, having a second DC bias voltage, e.g., +300 mV, after a settling period, a second current level is measured. The current levels may then be compensated based on the effective capacitance 110 of the biosensor cell 102 and used to determine a glucose level for the sample. This process will now be described in detail. The glucose concentration (G) can be calculated as follows:

$$G = \left(\frac{i_{ss}}{i_{fp}}\right)^p (G_{sp} - z); \quad (9)$$

where $i_{fp}$ is a first pulse current of one polarity determined during a first pulse (fp), $i_{ss}$ is a steady state pulse current of an opposite polarity determined during a second pulse (sp), p and z are calibration constants, and $G_{sp}$ is a glucose concentration calculated during the second pulse. The second pulse glucose concentration ($G_{sp}$) can be calculated as follows:

$$G_{sp} = \frac{d}{2FAD} i_{ss}; \quad (10)$$

where d is the thickness of the biosensor cell, F is Faraday's constant, A is the biosensor cell area, and D is the diffusion coefficient. In one embodiment, the first pulse current, $i_{fp}$, is determined during the first pulse just prior to the biasing voltage's transition from −300 mV to +300 mV and the steady state current, $i_{ss}$, is determined during the second pulse after the current level settles to a substantially constant level.

If the biosensor cell is not filled completely by the sample and the cell area equals A, then $G_{sp}$ and G can be calculated based on the partially filled volume. To illustrate this concept, assume a partially filled biosensor cell with the portion of the biosensor cell covered by the sample represented by partially filled area, $A_{PF}$, where PF stands for partially filled. In order to calculate the glucose value, this area is used to calculate the partially filled glucose value:

$$G_{PF} = \left(\frac{i_{ssPF}}{i_{ppPF}}\right)^p (G_{spPF} - z); \qquad (11)$$

where:

$$G_{spPF} = \frac{d}{2FA_{PF}D} i_{ssPF} \qquad (12)$$

Therefore, $$G_{PF} = \left(\frac{i_{ssPF}}{i_{fpPF}}\right)^p \left(\frac{d}{2FA_{PF}D} i_{ssPF} - z\right). \qquad (13)$$

The cell currents, $i_{ss}$ and $i_{fp}$, are proportional to the cell area A and the equivalent cell capacitance is proportional to the cell area:

$$\frac{i_{ssF}}{i_{ssPF}} = \frac{i_{fpF}}{i_{fpPF}} = \frac{A_F}{A_{PF}} = \frac{C_F}{C_{PF}}; \qquad (14)$$

where F stands for a completely filled cell.

Therefore, if the partially filled cell currents, $i_{ssPF}$ and $i_{fpPF}$, are calculated and substituted to calculate the glucose concentration of a sample that partially fills the biosensor cell, then:

$$G_{PF} = \left(\frac{i_{ssF} \frac{C_{PF}}{C_F}}{i_{fpF} \frac{C_{PF}}{C_F}}\right)^p \left(\frac{d}{2FA_{PF}D} i_{ssF} \frac{C_{PF}}{C_F} - z\right). \qquad (15)$$

If the ratio for capacitance is substituted with the ratio for area, then:

$$G_{PF} = \left(\frac{i_{ssF}}{i_{fpF}}\right)^p \left(\frac{d}{2FA_{PF}D} i_{ssF} \frac{A_{PF}}{A_F} - z\right); \qquad (16)$$

and $$G_{PF} = \left(\frac{i_{ssF}}{i_{fpF}}\right)^p \left(\frac{d}{2FA_F D} i_{ssF} - z\right). \qquad (17)$$

This is equivalent to the glucose calculated from a completely filled biosensor cell in equation 9, i.e.:

$$G_{PF} = G_F \qquad (18)$$

This indicates that an accurate glucose level can be calculated even if the biosensor cell 102 is only partially filled.

Figure 4:
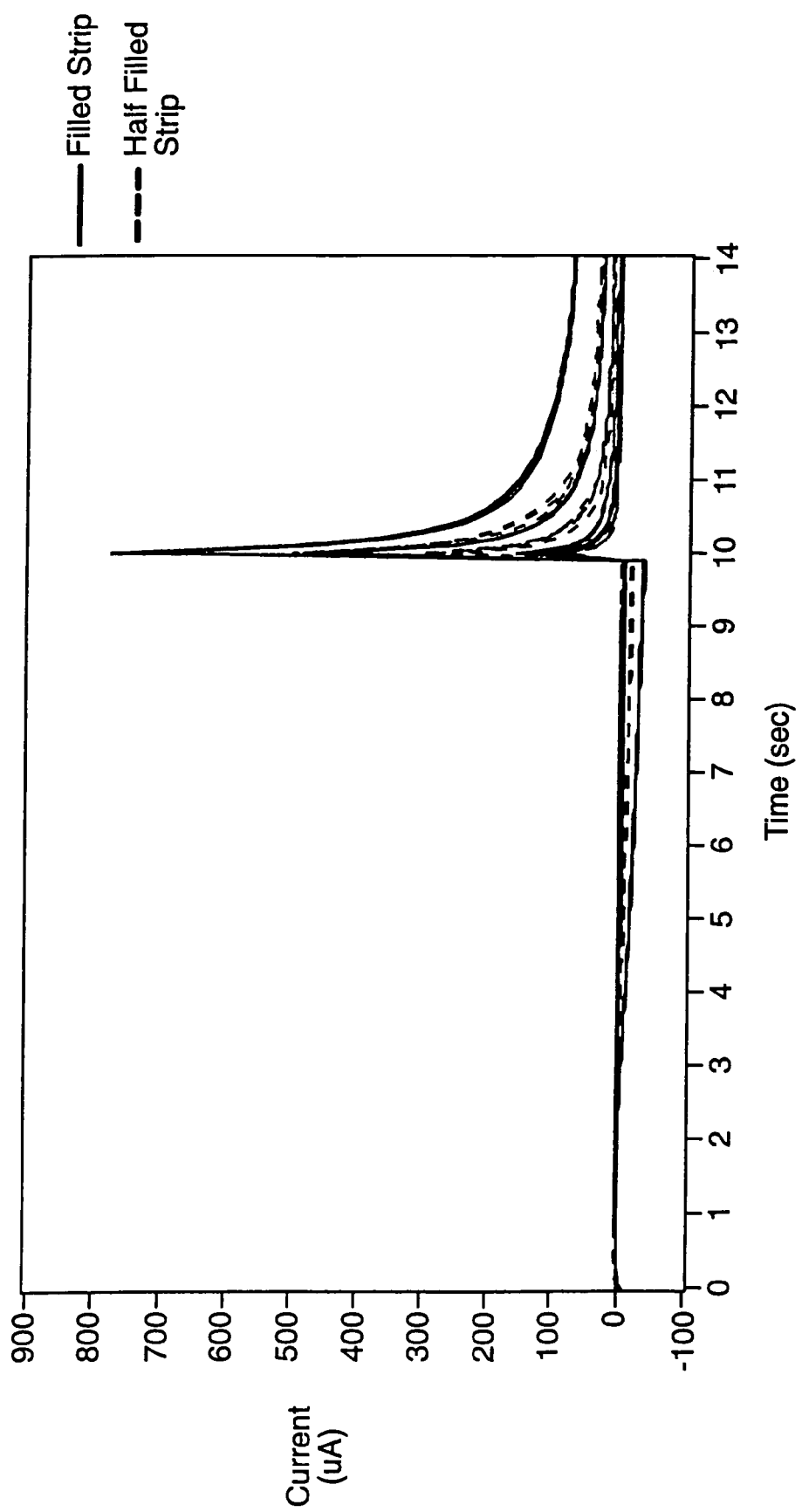
FIG. 4 is a graph depicting current values for filled and half-filled biosensor cells in accordance with the present invention.

FIG. 4 depicts pulse current values for filled and half-filled biosensor cells during first pulse and second pulse periods prior to compensation based on the effective capacitance of the biosensor cell in accordance with the present invention. The transition from first pulse to second pulse occurs at about 10 seconds in the example depicted in FIG. 4. As shown, the shapes of the current profiles are approximately the same for the filled and half-filled biosensor cells, however, there are significant differences in their current values. These differences may be due to variations in the actual glucose levels and the volumes of the samples. For example, a low glucose level calculation may be due to a low glucose level and/or a low sample volume. Therefore, glucose level calculations based on current levels prior to compensation may be inaccurate. Results shown in the FIG. 4 were collected by dosing biosensor cells with blood samples having 40 mg/dL to 600 mg/dL glucose and hematocrit levels of 20–70%.

Figure 5:
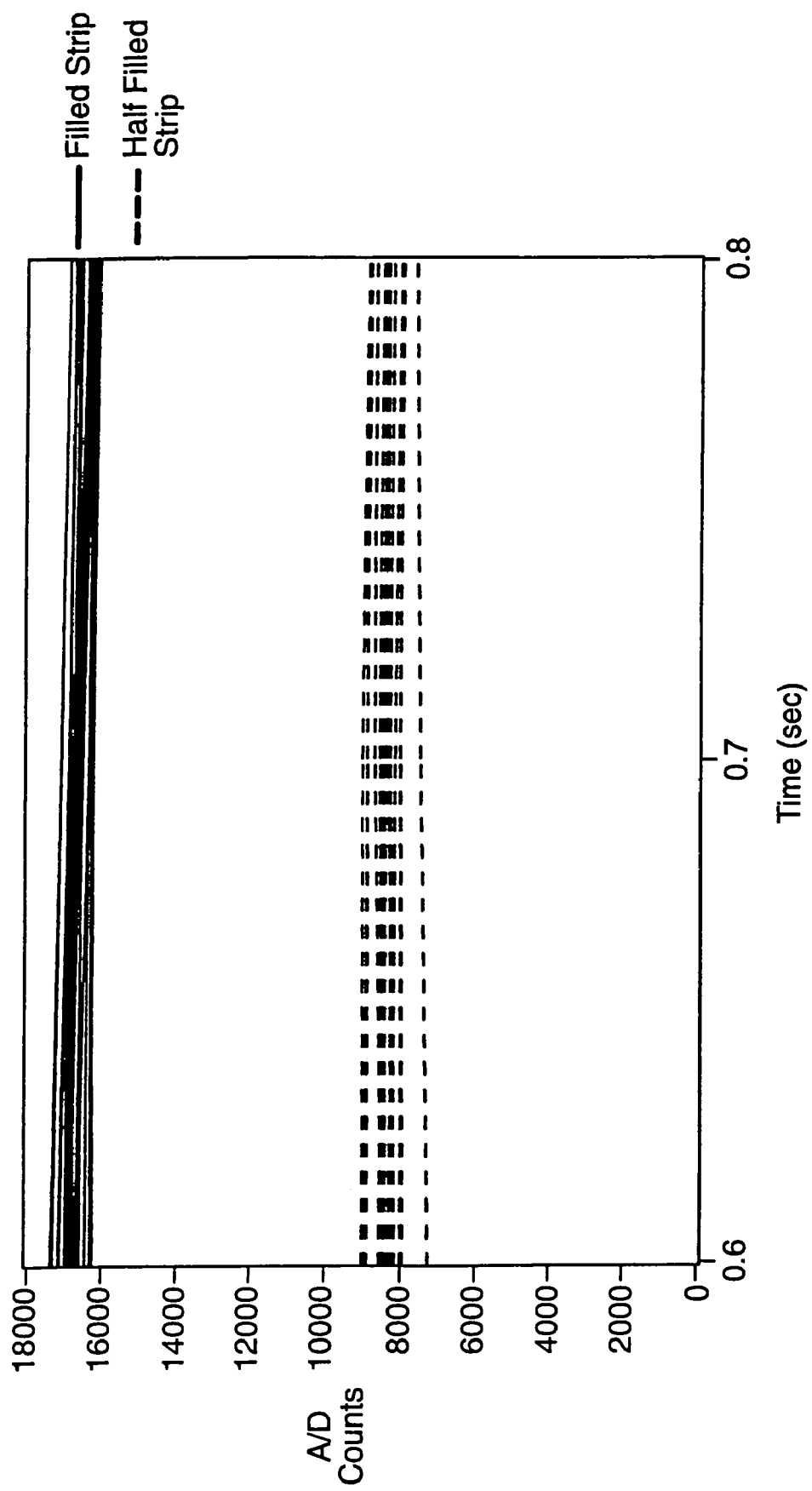
FIG. 5 is a graph depicting volume detection A/D readings for filled and half-filled biosensor cells in accordance with the present invention.

FIG. 5 depicts volume detection A/D readings for completely filled and half-filled biosensor cells during 0.6 to 0.8 seconds after a sample is detected in a known manner. A synthesized AC sine wave is applied at the beginning of the first pulse and the volume detection circuits are stabilized before obtaining volume detection A/D readings. As shown, A/D readings for half-filled biosensor cells are about half the A/D readings for filled biosensor cells, thereby demonstrating that the A/D readings are related to the volume of the sample within the biosensor cell. Results shown in FIG. 5 were collected by dosing biosensor cells with blood samples having 40 mg/dL to 600 mg/dL glucose and hematocrit levels of 20–70%.

Figure 6:
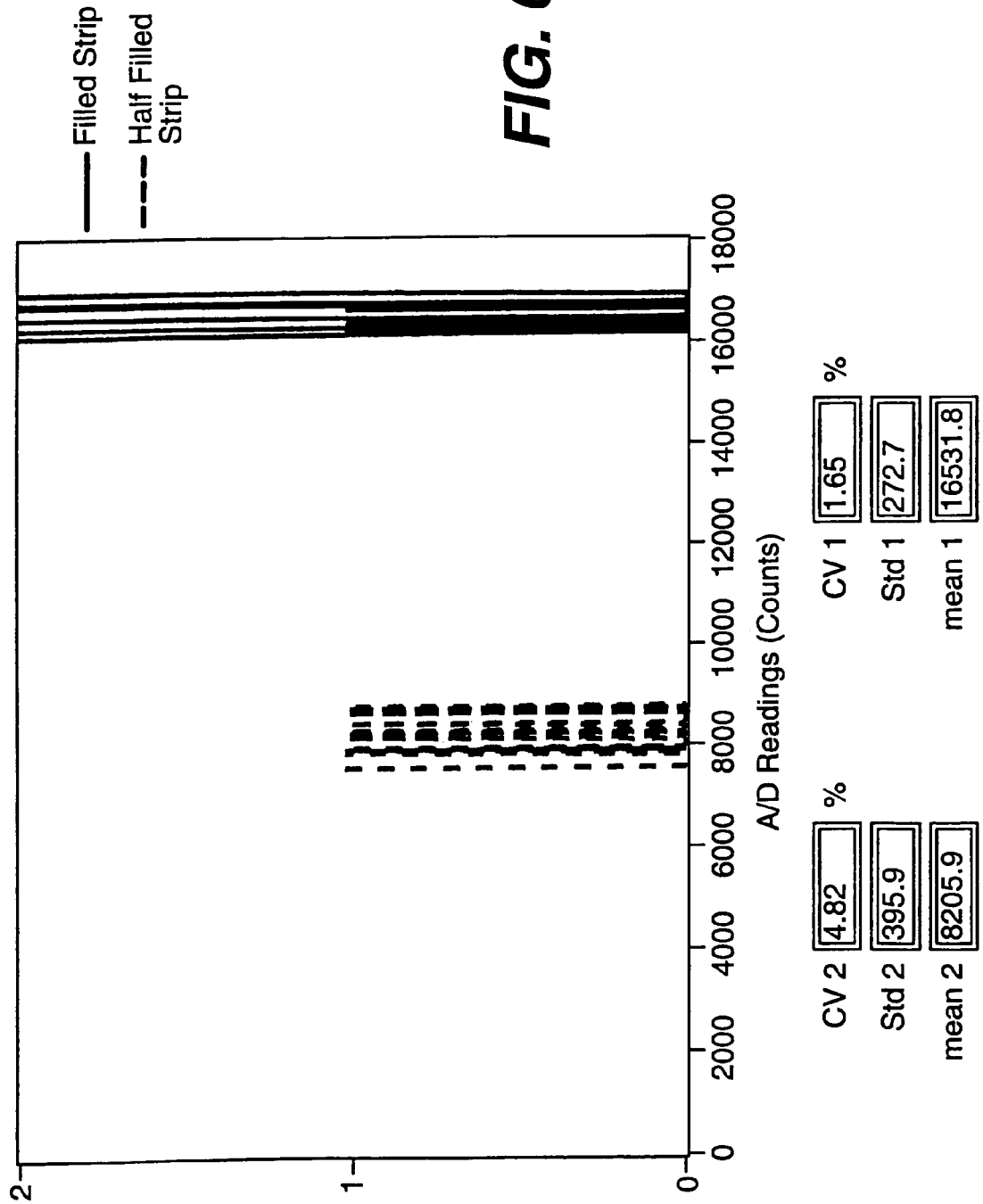
FIG. 6 is a graph depicting a histogram of A/D readings, mean, standard deviation, and coefficient of variation (CV) of filled and half-filled biosensor cells at 0.8 seconds after a sample is applied in accordance with the present invention.

FIG. 6 depicts a histogram of A/D readings, mean, standard deviation, and coefficient of variation (CV) of filled and half-filled biosensor cells at 0.8 seconds after a sample is detected. As shown, the A/D reading are strongly correlated to the sample volume.

Figure 7A:
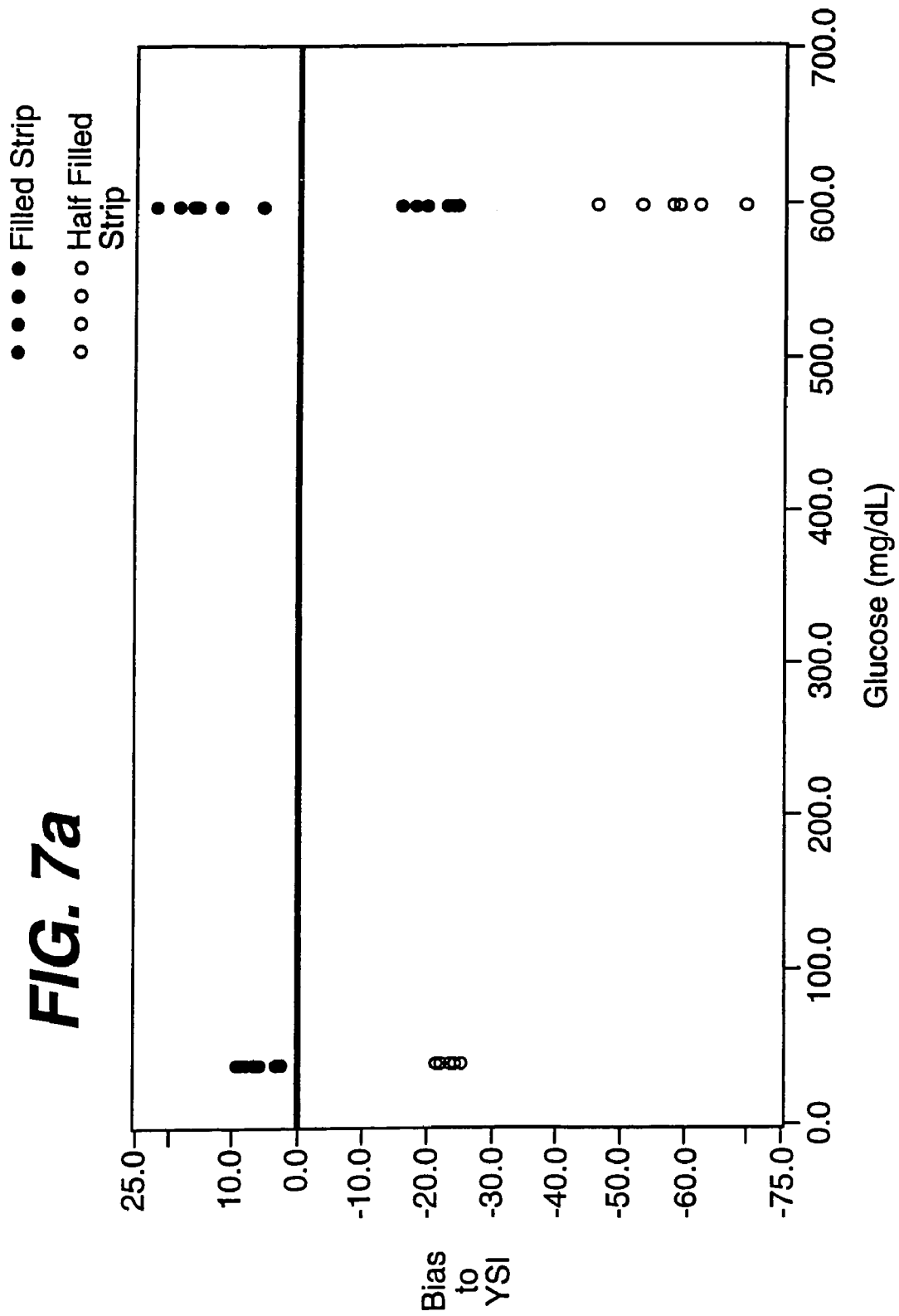
FIG. 7a is a graph depicting glucose biases compared to an industry standard prior to volume compensation in accordance with the present invention.
Figure 7B:
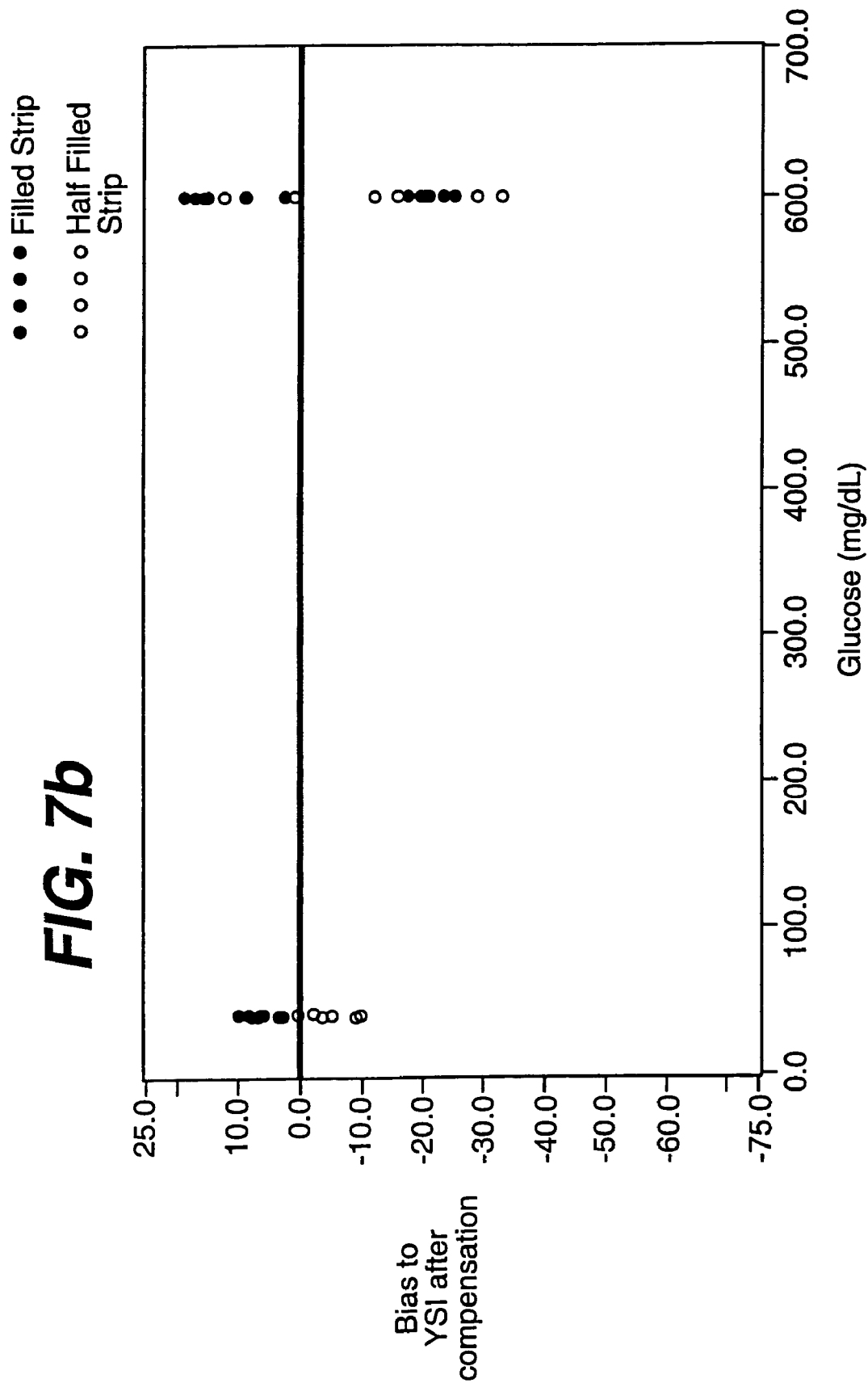
FIG. 7b is a graph depicting glucose biases compared to an industry standard after volume compensation in accordance with the present invention.

FIGS. 7a and 7b depict a comparison of the glucose biases of a biosensor in accordance with the present invention to glucose measurements performed by a YSI Glucose Analyzer available from YSI Incorporated of Yellow Springs, Ohio, USA (an industry recognized "gold" standard for performing glucose measurements) before and after compensation for sample volumes applied to the biosensor cell, respectively. The glucose biases represent the differences between glucose levels measured by a biosensor in accordance with the present invention and glucose levels measured by the YSI Glucose Analyzer at the glucose levels measured by the YSI Glucose Analyzer. In FIGS. 7a and 7b, when glucose levels measured by the YSI Glucose Analyzer are below 100 mg/dL the bias is defined in terms of mg/dL and when glucose levels measured by the YSI Glucose Analyzer are above 100 mg/dL the bias is defined in terms of a percentage.

FIG. 7a shows the glucose biases for completely filled and half-filled biosensor cells prior to being compensated by the volume detection A/D readings. As shown, the half-filled biosensor cells can have up to −70% bias for a sample having a glucose level of 600 mg/dL and −25 mg/dL bias for a sample having a glucose level of 40 mg/dL. FIG. 7b shows a significant improvement in the half-filled biosensor cell glucose biases after compensation with volume detection A/D readings. As shown, the half-filled biosensor cell's bias is reduced to less that approximately −30% for a sample having a glucose level of 600 mg/dL and −10 mg/dL for a sample having a glucose level of 40 mg/dL.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A glucose measurement method for use with a biosensor, said biosensor configured to receive a sample having a volume, said method comprising the steps of:
   determining the volume of the sample through synchronous demodulation when the sample is received by deriving the volume based on a signal that is proportional to an effective capacitance across the biosensor cell; and
   determining a glucose measurement for the sample if the volume is greater than a first level based on the determined volume of the sample.

2. The method of claim 1, further comprising the step of:
   detecting whether the sample is of a specific type; and
   storing the glucose measurement if the sample is said specific type.

3. A method for measuring glucose levels in a sample partially filling a biosensor cell, the biosensor cell having a filled effective capacitance, said method comprising the steps of:
   determining a partially filled effective capacitance for the sample;
   determining a first current level passing through the biosensor cell during a first pulse;
   determining a second current level passing through the biosensor cell during a steady state portion of a second pulse;
   multiplying said first current level by the ratio of the filled effective capacitance to said partially filled effective capacitance to generate a second compensated current level; and
   calculating a glucose level for the partially filled sample based on said first and second compensated current levels.

* * * * *